United States Patent [19]
Bohler et al.

[11] 3,984,772
[45] Oct. 5, 1976

[54] SIGNAL PEAK DETECTION ARRANGEMENT

[75] Inventors: Walter Bohler, Norwalk; Duane L. Smith, Fairfield, both of Conn.

[73] Assignee: The Perkin-Elmer Corporation, Norwalk, Conn.

[22] Filed: Nov. 4, 1974

[21] Appl. No.: 520,678

Related U.S. Application Data

[62] Division of Ser. No. 337,566, March 2, 1973, Pat. No. 3,854,818.

[52] U.S. Cl. ............................ 324/103 P; 324/130
[51] Int. Cl.² ........................................ G01R 19/16
[58] Field of Search ................... 330/9; 324/103 P, 324/130, 103 R

[56] References Cited
UNITED STATES PATENTS

| 3,105,230 | 9/1963 | MacIntyre | 324/130 |
| 3,412,241 | 11/1968 | Spence et al. | 324/103 P |
| 3,532,980 | 10/1970 | Tucker | 324/103 R |

Primary Examiner—R. V. Rolinec
Assistant Examiner—Ernest F. Karlsen
Attorney, Agent, or Firm—S. A. Giarratana; F. L. Masselle; J. M. O'Meara

[57] ABSTRACT

A method and apparatus is provided for compensating for repeatable error signal components which occur with information components. The method provides for detecting the peak amplitude of an error signal and providing a representation thereof, storing the representation, providing a composite electrical signal having the information and error components, detecting the peak amplitude of the composite signal and providing a representation thereof, and combining the stored error signal representation with the composite signal representation to provide an output signal from which the error signal component has been substantially removed.

3 Claims, 15 Drawing Figures

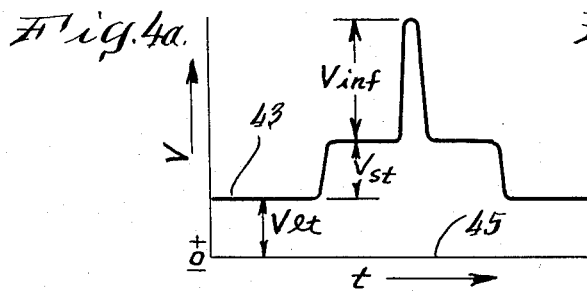
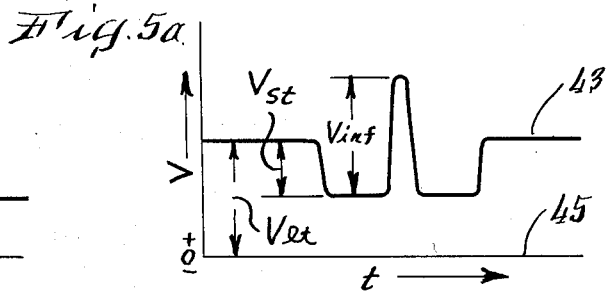
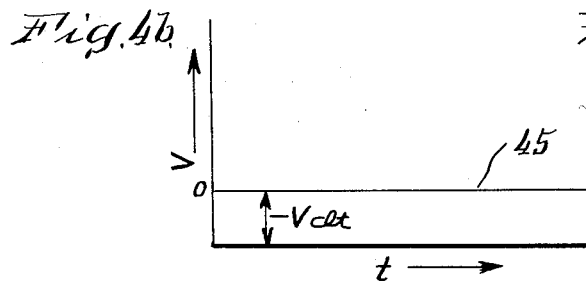
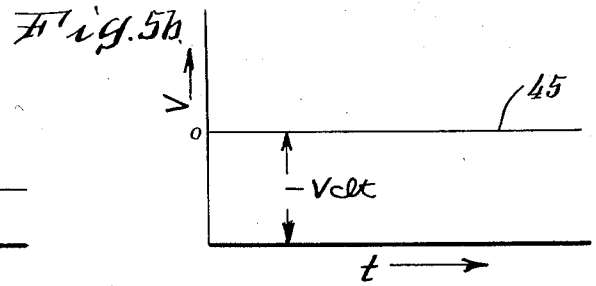
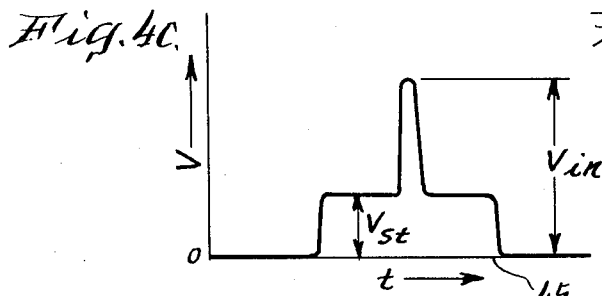
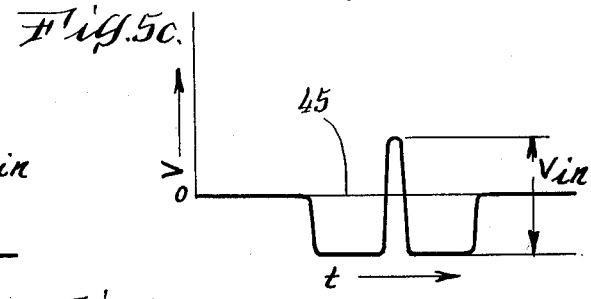
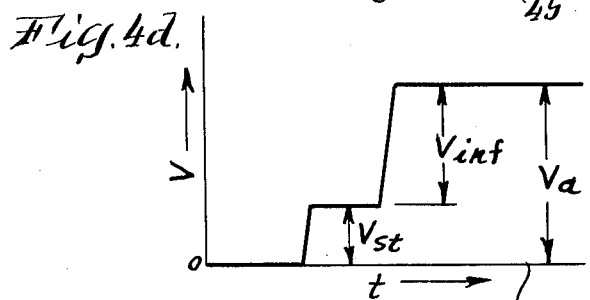
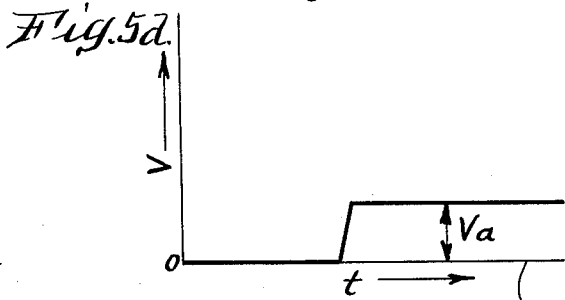
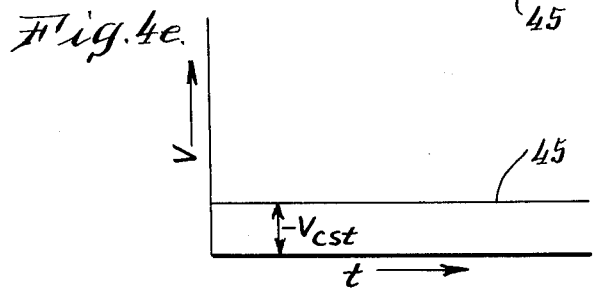
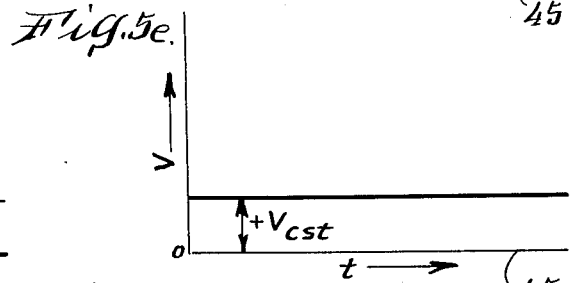
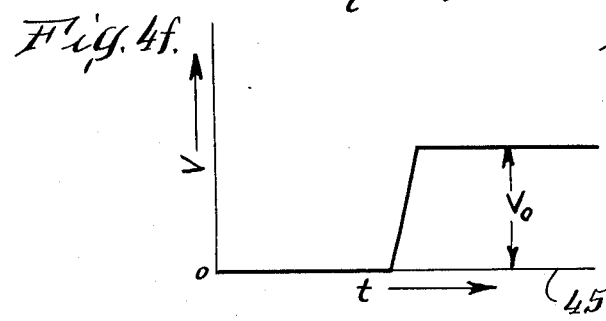
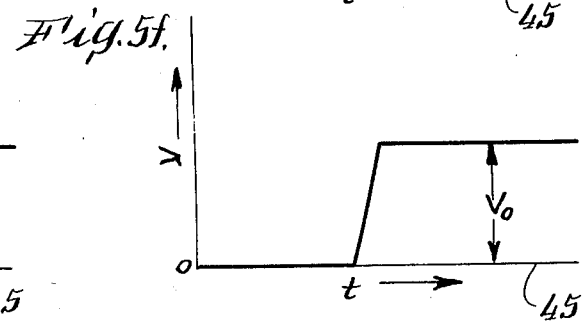

SIGNAL PEAK DETECTION ARRANGEMENT

BACKGROUND OF THE INVENTION

This is a division of copending U.S.A. Patent Application Ser. No. 337,566 filed Mar. 2, 1973 now U.S. Pat. No. 3,854,818.

This invention relates to electrical signal amplitude peak detecting arrangements. The invention relates more particularly to improvements in peak detecting means employed with analytical instruments.

This invention is described herein with reference to its application to an atomic absorption spectrometer for purposes of illustration; the circuit arrangement of this invention is adapted and intended for use with any type of instrument in which means for detecting electrical signal peak amplitudes, and for compensating error signal components, could beneficially be utilized.

The atomic absorption spectrometer is a known form of quantitative analytical instrument in which a sample is atomized in the presence of light energy of a limited predetermined spectrum. This spectrum corresponds to the absorption spectrum characteristics of a constituent material in a sample composition under analysis.

Absorption of light by the atomized constituent material is sensed by photodetection means and a corresponding electrical indication is thereby generated. The instrument includes means for providing an analog output signal having a peak amplitude which is representative of the absorbance and thus of the concentration of the material. This output signal is then applied to a display or a recording means such as a chart recorder which provides an indication from which the instrument operator can determine the concentration of the material in the sample composition.

It is at times desirable to provide an instrument output signal for use with digital equipment. This is desirable, for example, when the instrument output is to be analyzed by data handling equipment. Similarly, a digital signal is desirable in order to facilitate analysis by an instrument operator through the use of digital output displays and printers. One technique for the conversion of an analog signal of this type to digital form comprises sensing the peak amplitude of the analog instrument output signal and converting this amplitude into an equivalent digital representation. The accuracy of the digitized signal is, of course, largely dependent upon the accuracy with which the peak detection is accomplished.

Various factors such as changes in characteristics of components within the instrument and electrical noise contribute to inaccuracies in the peak amplitude of the output signal. These factors present themselves cumulatively as a deviation in the generally steady or relatively slowly varying baseline of the output signal from a desired reference level. Because these error deviations are of relatively long-term duration, the undesired baseline deviation can be readily corrected. The instrument operator accomplishes the correction by the adjustment of output signal zeroing or compensating means. The resulting baseline correction thus provides a substantially error free signal for conversion into digital form.

Improvements in the atomic absorption instrument, however, have resulted in the generation of a relatively short-term output signal which at times is preceded and followed by relatively short-term interference components. For example, although it is desirable to utilize a heated graphite atomizer form of furnace, it is known that this type of atomizer generates a short sample absorption output signal peak and a relatively short-term interference component which immediately precedes and follows the output signal peak. These interference components alter the peak amplitude of the signal with respect to the reference level and thereby introduce an error into the signal. In view of the relatively short-term nature of these error-introducing components, it is not feasible and generally not possible for the instrument operator to readjust the zeroing means in order to compensate for these short-term deviations from the reference level.

Accordingly, it is an object of this invention to provide an improved method and means for detecting the peak amplitude of an electrical signal.

Another object of this invention is to provide a peak detecting method and means adapted for compensating for relatively short-term interference or error signal components which accompany the occurrence of an information signal.

Another object of the invention is to provide a peak-detecting means adapted for compensating for relatively short-term positive or negative interference or error signal components.

Another object of the invention is to provide an improved peak detecting method and means adapted for compensating for repeatable, relatively short-term interference or error signal components of substantially constant amplitude.

In accordance with the peak detection method of this invention, a repeatable error signal of relatively short-term duration is derived from an information signal source and is applied to an input terminal of a peak detection arrangement. The peak amplitude of this error signal is detected and a representation thereof is stored. An information signal and the repeatable error signal are subsequently coincidentally derived from the information signal source and are applied to the input terminal of the peak detection arrangement. The peak sum of these signals is detected and is altered in accordance with the amplitude of the stored representation in order to provide a peak detected information output signal from which the amplitude of the short-term error signal is substantially removed.

In accordance with features of the peak detection arrangement of this invention, a circuit means is provided for detecting and providing a signal $V_d$ representative of the peak amplitude of an input signal $V_{in}$ which is applied thereto. Circuit means are provided for selectively storing a representation of the amplitude of the signal $V_d$ and for altering the detected peak amplitude of a subsequently applied input signal in accordance with the amplitude of the stored representation to provide an output information signal $V_o$ which is corrected for error or interference components. In accordance with more particular features of the peak detection arrangement of this invention, the storage and amplitude altering circuit means is adapted for automatically combining the peak amplitude of a stored error signal $V_{est}$ in phase opposition with the peak detected signal $V_d$ corresponding to a subsequently applied input signal to thereby provide an output information signal $V_o$ from which repeatable, short-term error signal components are substantially removed.

In accordance with further features of the invention, a peak detection circuit arrangement comprises circuit means for detecting error signal components of relatively positive and negative polarity of the error signal component of larger absolute amplitude, and for effecting combination of the stored representation with a subsequently detected composite signal having information and error signal components in a manner for substantially removing the error signal component of the composite detected signal.

These and other objects and features of the invention will become apparent with reference to the following specification and to the drawings wherein:

FIGS. 4a–4f are diagrams illustrating the waveforms occurring in the spectrometer of FIG. 1; and, FIGS. 5a–5f are diagrams illustrating alternative waveforms occurring in the spectrometer of FIG. 1.

Figure 1:
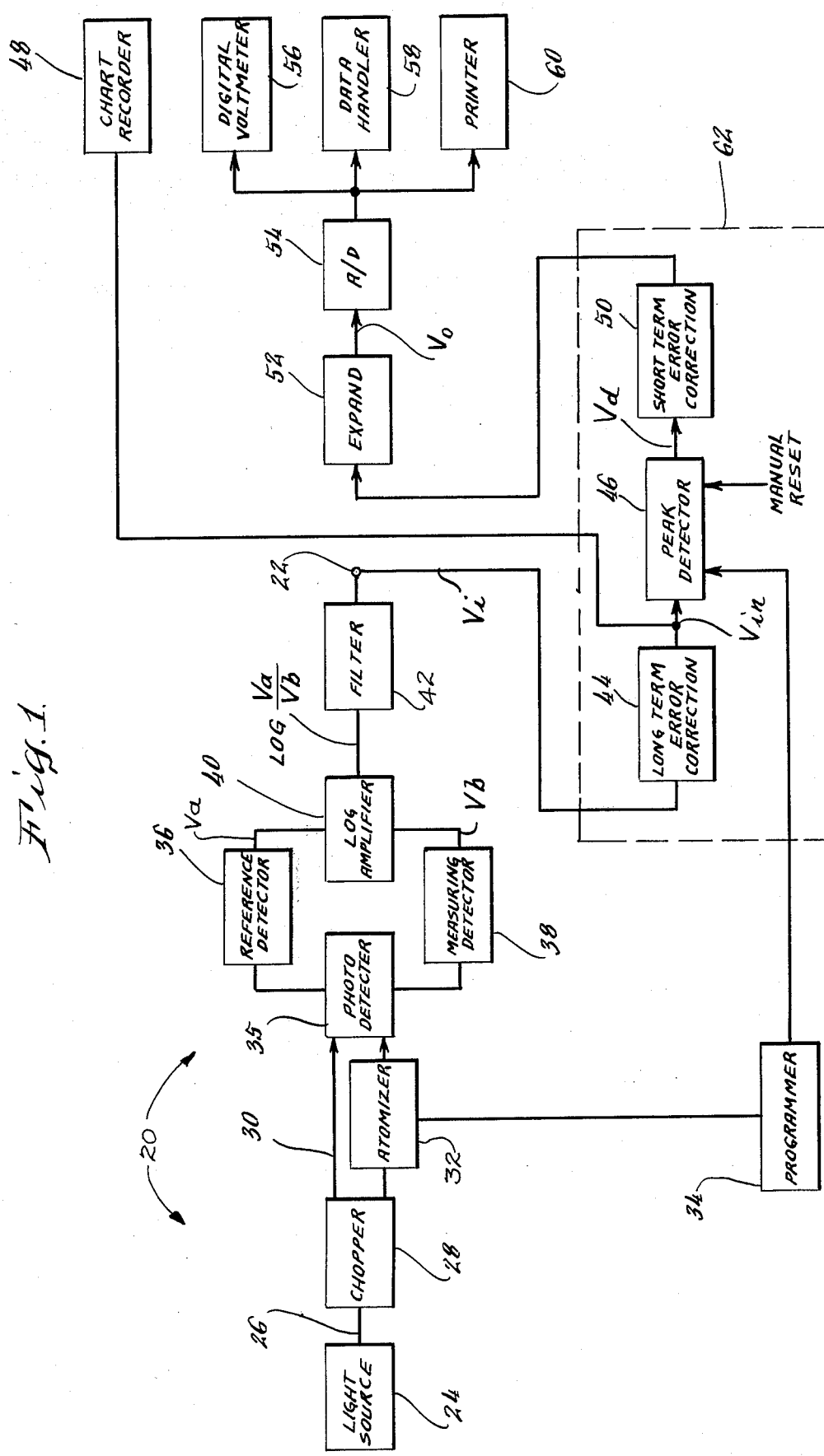
FIG. 1 is a block diagram of an atomic absorption spectrometer which provides peak detection correction in accordance with the present invention.

Referring now to FIG. 1, an atomic absorption spectrometer is shown to include a known arrangement referenced generally as 20 for providing at a terminal 22 an electrical signal $V_i$ which is representative of the absorbance of a sample material under analysis. The spectrometer includes a light source 24 which generates a light beam 26 having a predetermined limited spectrum corresponding to an absorption spectrum of a sample under analysis. The light beam 26 is projected toward an optical chopper 28 which phase or time divides the projection of the light beam between a reference projection path 30 and a measuring path extending through a sample atomizer 32. While various atomizers have been employed with atomic absorption spectrometers, the atomizer 32 preferably although not exclusively comprises a heated graphite atomizer. This form of atomizer generally comprises an electrically heated furnace within which the sample material is positioned for heating and atomizing. The heated graphite atomizer 32 is heated in a programmed sequence of steps which progressively increase the temperature of the sample material. Under the control of a program control means 34, the atomizer 32 is initially heated to a temperature on the order of about 100°C. for dehydrating the sample material. The atomizer is next heated to a temperature on the order of about 1000°C. in order to carbonize and burn off undesired organic components of the material under analysis. Finally, the atomizer is elevated in temperature for a relatively short interval of time in order to atomize the sample material for the purpose of spectrum absorption examination. The beam which travels along a reference path 30 and the beam which is projected through the atomizer 32 impinge upon a photodetection means 35 which may comprise a photomultiplier. An output signal from this photodetector is applied to a phase sensitive reference detector 36 and to a phase sensitive measuring detector 38. Output signals $V_a$ and $V_b$ from the detectors 36 and 38 respectively are applied to an amplifying circuit means 40 which forms the logarithm of the ratio of the signals $V_a/V_b$. The logarithm $V_a/V_b$ is proportional to the absorbance of the material under analysis. The amplified information signal is coupled from the amplifier 40 to the terminal 22 through a filter network 42. The operation of an atomic absorption spectrometer is well known and is described in greater detail in U.S. Pat. No. 2,847,899.

The instrument signal $V_i$ at the terminal 22 comprises, as indicated, an information signal which is representative of the absorbance of the sample material. This signal, in addition to containing an information component $V_{inf}$ extending from a baseline component 43, may also include a relatively long-term error component $V_{lt}$ (FIGS. 4 and 5) which causes a deviation of the baseline component 43 from a reference level 45, such as ground potential in FIGS. 4 and 5. This, of course, is undesirable since it alters the peak amplitude of the information signal with respect to the reference level and detracts from the acccuracy of the information signal. Circuit means have heretofore been provided which enable the instrument operator to compensate for this deviation. However, it is known that in certain instances, an interference signal component $V_{st}$ of relatively short-term duration occurs which, because of its short-term characteristic, is not susceptible to compensation through adjustment of the instrument by the operator. A short-term component for the purposes of this specification and appended claims occurs for an interval of time which is insufficiently long in duration to allow an instrument operator to recognize its occurrence and to accurately readjust the baseline 43 of the information signal. A typical short-time interval is on the order of 20 seconds or less. This is true, for example, when employing the heated graphite atomizer 32. It is known that this type of atomizer generates a relatively short-term interference component when the sample material is being cycled through the different heating steps leading to and culminating in atomization of the material. This interference component, in addition to occurring coincidentially in time with the information signal generally precedes and succeeds the information signal for a short interval of time.

The composite signal referred-to thus far is illustrated in FIG. 4a and in FIG. 5a. A reference level 45 is indicated in these Figures as 0 volts which comprises, for example, ground potential. The voltage $V_{lt}$ represents the relatively long-term deviation component of the signal baseline 43 from the reference level resulting from variations in circuit components and electrical noise. The voltage $V_{st}$ represents the relatively short-term error component which occurs coincidentally in time with the information component $V_{inf}$ and which generally precedes and succeeds this information component. While in FIG. 4a the short-term error component $V_{st}$ is shown to be relatively positive with respect to the baseline 43, it may also be relatively negative as illustrated in FIG. 5a. An important characteristic of the short-term interference signal component $V_{st}$ is its repeatability and its substantially constant amplitude during the coincidental occurrence with the information component $V_{inf}$. This component is principally attributable to operation of the heated graphite atomizer 32 and occurs during operation of the atomizer both in the presence and absence of sample material.

It is desirable to provide an instrument signal $V_i$ at the terminal 22 in a form which can be employed as an input signal to a chart recorder or in a form which can be converted into a digital representation for use in digital display, printing or data handling equipment. A peak detecting means is provided for detecting the peak amplitude of the information signal and for providing an analog or DC signal $V_d$ which can be converted into a digital signal. An accurate presentation of the information signal is accomplished only after correcting the signal for the referred-to error components.

To this end, the information signal and accompanying error signals are applied to a relatively long-term error signal correcting circuit means 44 which removes the long-term error signal component $V_{lt}$ from the composite signal waveform. The corrected signal $V_{in}$ is applied to a peak detecting circuit means 46 and to a chart recording means 48. Since the long-term signal component is compensated for by the circuit means 44, the chart recorder 48 will provide a record of the information signal and any short term component as is illustrated in FIGS. 4c and 5c. When employing the chart recorder, the instrument operator can then visually determine the short-term error component and compensate for this component when making a sample concentration determination.

The peak detected signal, however, must be corrected for short-term error components prior to conversion into digital form or the peak detected signal will undesirably include both information and short-term error components, i.e., in FIG. 4a, $V_{inf} + V_{st}$ and in FIG. 5a, $V_{inf} - V_{st}$. In accordance with a feature of the invention, the peak detecting arrangement is adapted for compensating for these short-term error signal deviations. To this end, the peak detector arrangement includes in addition to the peak detector 46, a short-term error correcting circuit means 50 which provides as an output signal a DC level which is proportional to the peak amplitude of the information and which is free of the short-term error signal component. This arrangement is discussed in further detail hereinafter. The corrected information signal, which is to be used for digital applications is applied to an expansion circuit means 52 which is adapted for adjusting the output signal to an absolute concentration value. This signal is then applied through an analog-to-digital converter 54, either simultaneously or alternatively, to a digital voltmeter display 56, to digital data handling equipment 58, and to a printer 60.

Figure 2:
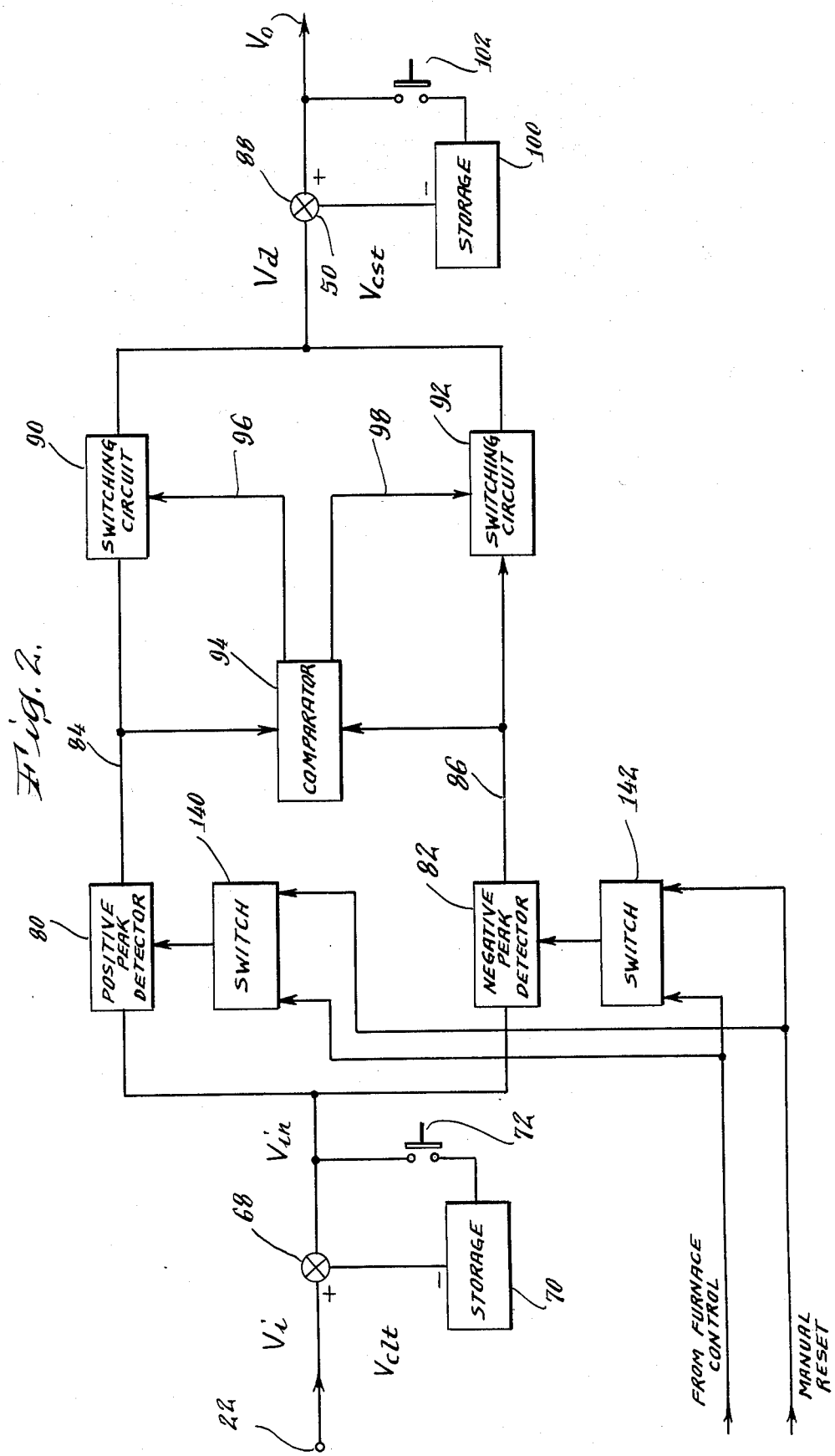
FIG. 2 is a block diagram in greater detail of a peak detecting and error signal correction means of FIG. 1.

The peak detector and the error signal compensating means, which are enclosed within the dashed rectangle 62 of FIG. 1, are illustrated in greater detail in FIG. 2. The long-term error component correction means 44 includes a signal combining means 68 to which is applied the input signal $V_i$ from the terminal 22 and an output voltage level from a signal storage means 70. A switching means 72 is provided for applying a voltage $V_{in}$ of the signal combining means 68 to an input terminal of the signal storage means 70. During the occurrence of a long-term error signal, the switch 72 is momentarily closed by the instrument operator and the amplitude of this long-term signal is applied to a storage means 70. The occurrence of a long-term error signal is indicated by the chart recorder and by the digital output indicators. The storage means 70 is adapted for applying to the signal combining means 68 a signal of the same magnitude but in phase opposition to thereby provide a long-term error corrected signal $V_{in}$ at the output of the signal combining means 68.

The long-term error corrected signal $V_{in}$ is simultaneously applied to a peak detecting circuit means which comprises a first peak detector 80 which is adapted for peak detecting the amplitudes of positive going signals and to a second peak detector 82 which is adapted for peak detecting the amplitudes of negative going signals. A DC potential proportional to the larger amplitude output of these detectors is alternatively applied to a signal combining means 88 through switching circuit means 90 or 92 respectively. The switching circuit means 90 and 92 each comprise gate circuits which enable or inhibit the transfer of the detected output $V_d$ from the detectors 80 and 82 respectively in accordance with a control input signal applied thereto from a comparator circuit means 94. Output signals from the detectors 80 and 82 are applied to the comparator 94. The comparator is adapted for comparing and determining which of the input signals is of the greater absolute amplitude and for enabling the corresponding switching circuit means while disabling the other switching circuit means. For example, when the DC level output from the peak detector 80 is greater in absolute amplitude than the output from the detector 82, the comparator 94 will provide an input control voltage over a line 96 to the switching circuit 90 for enabling the circuit 90 thereby coupling the output of the detector 80 to the signal combining circuit 88. The comparator 94 will simultaneously provide an inhibiting signal over line 98 which inhibits the coupling of the output of the detector 82 to the signal combining means 88.

Compensation for a relatively positive or a relatively negative short-term signal is provided. Polarity as well as amplitude compensation is effected by applying the peak detected signal $V_d$ of greater amplitude to a signal storage means 100 of the short-term error correcting circuit means 50. The detected signal $V_d$ which is applied to the signal combining means 88 is selectively applied to an input terminal of the storage means 100 by a switching means 102. An output voltage from the storage means is applied in phase opposition and combined with the signal $V_d$ for compensating for the short-term component.

The signal combining means 68 and 88 may comprise a resistive summing network or other form of arrangement for combining the stored error indication with the signal $V_i$ or $V_d$ respectively to provide an error corrected signal. These signal combining means can alternatively comprise a servomechanism including potentiometer having an adjustable or sliding contact which is operated in direction and magnitude by a motor in accordance with the stored error representation.

The operation of the circuit arrangement of FIG. 2 can be understood with reference to FIGS. 4 and 5 of the drawings. As indicated hereinbefore, a signal of the atomic absorption spectrometer which contains information and short and long term error components can have a composite waveform as illustrated in FIG. 4a. In the absence of the information and short-term error signal components and during the occurrence of the long-term error component $V_{lt}$ as illustrated at 43 in FIG. 4a, the switch 72 of the long-term error correction means 44 is closed and a potential equal in magnitude to the potential $V_{lt}$ is applied to the storage means 70. The storage means 70 is adapted for applying to the signal combining means 68 a correction signal $V_{clt}$ of opposite phase to the input signal $V_i$. A correction signal $V_{clt}$ which is applied to the combining circuit 68 is illustrated in FIG. 4b as $(-V_{clt})$. The sum of this error correcting signal and the long-term error signal results in the cancellation of the long-term error signal at the output of the signal combining network 68.

The long-term error-corrected signal $V_{in}$, corresponding to the signal of FIG. 4a, and which is applied to the peak detectors 80 and 82 and to the chart recorder 48 is illustrated in FIG. 4c. The equivalent signal of FIG. 5a is illustrated in FIG. 5c. It will be noted that in order to remove the relatively short-term error component $V_{st}$ with the arrangement described, a voltage level substantially equivalent to $V_{st}$ is stored by the storage circuit means 100. This voltage is stored preliminarily to the operation of the spectrometer during its sample test mode. A repeatable error signal is initially applied to the peak detectors and then to the storage means 100. In the operation of the atomic absorption spectrometer, the atomizer 32 is programmed with a blank sample container through a complete cycle. The interference noise and background noise which is generated when a sample is tested is also generated in the absence of the sample and comprises a repeatable signal of substantially the same constant amplitude. When the atomizer 32 is programmed through its cycle, the error signal is generated without information components. It is peak detected and stored by the storage means 100 for use as a compensating signal during the occurrence of the short-term component which generally precedes, coincides with and succeeds the information component. The error signal is stored by momentary closure of the switch 102 by the instrument operator during the atomizer cycling. This correction signal ($-V_{cst}$) is illustrated in FIG. 4e. Application of the signal waveform of FIG. 4c to the detectors 80 and 82 will result in a DC level proportional to the sum of the peak potentials $V_{inf} \div V_{st}$ at the output line 84 (FIG. 4d). Since the peak detector 82 is negatively polarized, there is no output on the line 86 from this detector. The comparator 94 will enable the switching circuit means 90 and cause the application of the potential from the detector 80 to the signal combining means 88. The signal combining means 88 to which the correcting voltage ($-V_{cst}$) is applied will provide an output signal $V_O$ as illustrated in FIG. 4f. The potential $V_O$ of FIG. 4f represents a DC potential which is error corrected for both the long and short term errors and is an accurate analog representation of the absorbance of the sample material.

Under conditions wherein the short-term error signal is relatively negative going, as illustrated in FIG. 5a, a relatively positive error correction signal $V_{cst}$ will be applied to error correction circuit 88 from the storage means 100. The relatively repeatable negative going error signal is sensed by the detector 82 and is applied to the storage means 100 through the switching means 92, the signal combining means 88 and the switching means 102 during the cycling of the atomizer 32 with a blank. During the occurrence of a subsequent signal $V_i$ which includes an information signal $V_{inf}$ at the terminal 22, an input signal $V_{in}$ to the detectors 80 and 82 will have a waveform as illustrated in FIG. 5c. The output $V_d$ of the positive peak detecting circuit 80 (FIG. 5d) will be applied through the switching circuit means 90 to the signal combining means 88 wherein it will be combined with the error correction voltage ($+V_{cst}$) to provide a corrected output signal $V_O$ as illustrated in FIG. 5f.

Figure 3:
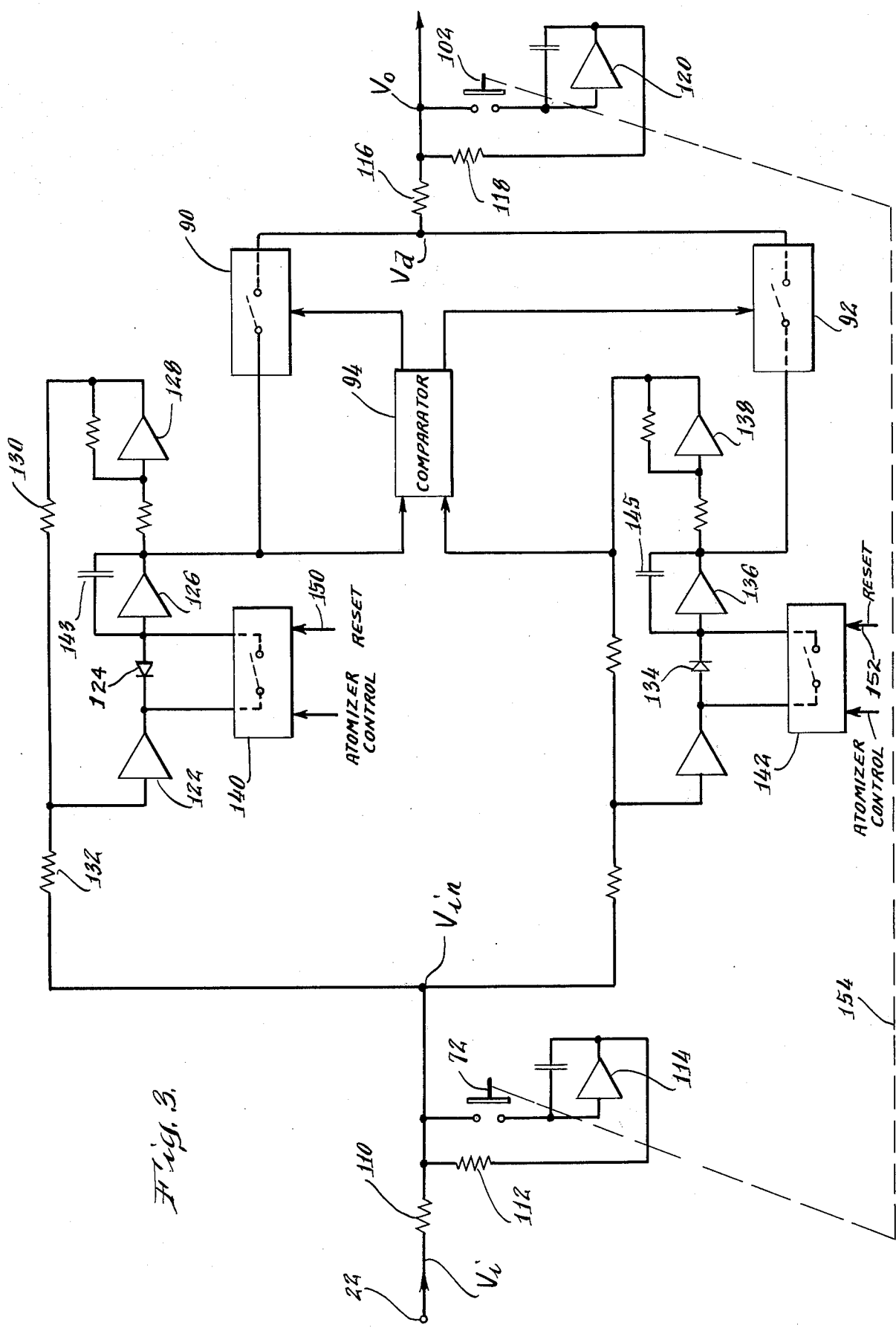
FIG. 3 is a schematic diagram, partly in block form, of the peak detecting and compensating signal means of FIG. 2.

A more detailed schematic diagram of the error correcting and peak detecting circuit arrangement is illustrated in FIG. 3. The signal combining means 68 of FIG. 2 is shown in FIG. 3 to comprise a resistive summing network including resistive impedances 110 and 112 while the storage means 70 is shown to comprise an operational amplifier 114 which is coupled for operating as an integrator. Similarly, the signal combining means 88 is shown to comprise a resistive summing network including resistive impedances 116 and 118 while the storage means 100 comprises an operational amplifier 120 arranged for operation as an integrator.

The positive peak detector 80 is formed by an operational amplifier 122, a diode 124, an operational amplifier 126 arranged for operation as an integrator, and an operational amplifier 128 having feedback for providing a gain of one. Feedback between the amplifier 128 and the input of amplifier 122 is provided by a resistive impedance 130. The input impedance to the amplifier 122 is provided by resistance 132. An output voltage level which is derived from the output of amplifier 126 is applied both to the comparator 94 and to the circuit switching means 90. The comparator circuit 94 comprises a circuit arrangement which is well known in the art. Reference is made to Millman and Taub, Pulse and Digital Circuits, McGraw Hill, 1956, for a more detailed explanation of the construction and operation of comparator circuit arrangements. The switching means 90 preferably comprises an electronic switch such as a field effect transistor arranged for operation as a gate.

The negative peak detector 82 is, as illustrated, constructed in a manner similar to the positive peak detector 80. However, it is noted that a diode 134 of this detector is oppositely polarized with respect to the diode 124 of the detector 80 thereby providing a negative polarity sensing peak detector. The negative output from an operational amplifier 136 arranged as an integrator is applied through the switching means 92 which, as in the case of the switching means 90, may comprise a field effect transistor switch. In order to provide an input signal to the comparator 94 having a polarity similar to the output of the integrator 126, the inversion provided by the operational amplifier 138 is utilized for phasing this input signal to the comparator 94.

In accordance with another feature of this invention, a means is provided for controlling the peak detectors for operation only during the atomizing portion of the sample heating. The programmer 34 (FIG. 1) provides a control signal which is applied to switching means 140 (FIG. 3) of the peak detector 80 and to the switching means 142 of the peak detector 82. These switching means are arranged for disabling the peak detector under the control of the signal from the furnace and additionally, as illustrated for providing a manual reset for the detector arrangement. The switches 140 and 142 may comprise field effect transistors which are controlled by signals from the atomizer programmer control or by a manual reset switch. By effecting the closure of the switch, the diodes 124 and 134 are bypassed thereby inhibiting the feedback capacitors 143 and 145 of the operational amplifiers 126 and 136 respectively from storing a charge. Release or opening of the switch 140 or 142 restores the back impedance of these diodes into the circuit and permits the capacitors to take a charge and the circuit to function as a peak detecting circuit. The switches 140 and 142 additionally have applied thereto control signals from a manual reset switch through control lines 150 and 152 respectively. These reset switches enable the instrument operator to discharge the integrator capacitors and reset the state of the peak detectors. The circuit arrangement can be employed in a non-peak detecting, one-to-one amplifying mode by maintaining the switches 150 and 152 in a closed condition for bypassing the diodes 124 and 134. A manual coupling represented by the dashed line 154 is provided for simultaneously operating the switches 72 and 102. When the switches 72, 102, 140 and 142 are closed in the amplifying mode of operation, the output voltage $V_O$ will track the input voltage $V_{in}$. The switches 72 and 102 are alternatively independently operable for selectively storing error component representations.

There has thus been described an improved method and apparatus for signal amplitude peak detection and an improved atomic absorption spectrometer which advantageously provides a relatively accurate output DC analog representation of information components and which has been corrected for relatively short-term interference components.

While there have been described particular embodiments of this invention, it will be appreciated that various modifications may be made thereto without departing from the spirit of the invention and the scope of the appended claims.

What is claimed is:

1. A peak detecting circuit arrangement for compensating for repeatable, relatively short-term error signal components of a composite signal having relatively short-term information and error components comprising:

circuit means having a terminal thereof for detecting and providing a signal representative of the peak amplitude of an input signal applied to said terminal;

storage circuit means for storing a signal applied thereto;

means intercoupling said circuit storage means and said peak detecting circuit means for combining said stored signal in phase opposition with the signal representation of said peak detector means to provide an output signal thereof; and, means for selectively coupling an output signal from said signal combining means to said circuit storage means for selectively storing said output signal in said signal storage means, said peak detection circuit means including polarity sensitive means for detecting the polarity of an applied signal and for providing a signal representative of the peak amplitude and polarity of an applied signal for providing that the stored signal is recombined in phase opposition with a subsequently applied signal.

2. The detection arrangement of claim 1 wherein said peak detector comprises a firt peak detector adapted for detecting the peak amplitude of an input signal of a first predetermined polarity;

a second peak detector adapted for detecting the peak amplitude of an input signal of a second opposite polarity;

switching means responsive to an input signal for alternatively coupling the output signals from said first and second detectors to said signal combination means;

comparator circuit means for comparing the amplitude of the output signals from said first and second detectors and for applying an enabling control signal to the switching means associated with the peak detector providing the larger output signal and for disabling the switching means associated with the peak detector providing an output signal of lesser magnitude.

3. The detection arrangement of claim 2 wherein said storage means comprises an operational amplifier having input and output terminals, said operational amplifier having capacitive feedback means for causing said operational amplifier to operate as an integrating amplifier, means coupling said amplifier output terminal to said signal combining means, and switching means for coupling the output of said signal combining means to the input terminal of said amplifier.

* * * * *